United States Patent
Brandi et al.

[11] Patent Number: 5,670,523
[45] Date of Patent: Sep. 23, 1997

[54] METHODS OF INHIBITING MUSCULOAPONEUROTIC FIBROMATOSES (DESMOID TUMORS)

[75] Inventors: Maria Luisa Brandi; Francesco Tonelli, both of Florence, Italy

[73] Assignee: Eli Lilly and Company, Indianapolis, Ind.

[21] Appl. No.: 780,656

[22] Filed: Jan. 7, 1997

Related U.S. Application Data

[60] Provisional application No. 60/010,773 Jan. 29, 1996.
[51] Int. Cl.[6] .................. A61K 31/445; A61K 31/38
[52] U.S. Cl. ............................. 514/324; 514/443
[58] Field of Search .................. 514/324, 443

[56] References Cited

U.S. PATENT DOCUMENTS

| | | |
|---|---|---|
| 4,418,068 | 11/1983 | Jones . |
| 5,393,763 | 2/1995 | Black et al. . |
| 5,457,116 | 10/1995 | Black et al. . |
| 5,574,047 | 11/1996 | Bumol et al. . |

FOREIGN PATENT DOCUMENTS

| | | |
|---|---|---|
| 652004 | 5/1995 | European Pat. Off. . |

OTHER PUBLICATIONS

Hayry et al., Am. J. Clin. Pathol. 77(6), pp. 681-685 (Biosis abstract No. 75035377). 1982.
Sportiello et al., Cancer 67, No. 5, pp. 1443-1446 (Derwent abstract No. 91-16264) 1991.
Evans et al., Endocrinology 134(5), pp. 2282-2288 (Biosis abstract No. 97274419). 1994.

*Primary Examiner*—Raymond Henley, III
*Attorney, Agent, or Firm*—James J. Sales; David E. Boone

[57] ABSTRACT

A method of inhibiting musculoaponeurotic fibromatoses comprising administering to a mammal in need thereof an effective amount of a compound having the formula

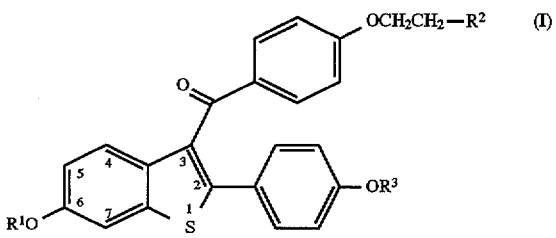

wherein $R^1$ and $R^3$ are independently hydrogen,

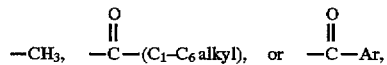

wherein Ar is, optionally substituted phenyl;

$R^2$ is selected from the group consisting of pyrrolidine, hexamethyleneimino, and piperidino; or a pharmaceutically acceptable salt of solvate thereof.

4 Claims, No Drawings

METHODS OF INHIBITING MUSCULOAPONEUROTIC FIBROMATOSES (DESMOID TUMORS)

This application claims the benefit of U.S. Provisional Application Ser. No. 60/010,773, filed Jan. 29, 1996

BACKGROUND OF THE INVENTION

The musculoaponeurotic fibromatoses are a group of nonmetastasizing, locally invasive dysplastic lesions of connective tissue. Included in this group are nodular fasciitis, plantar fibromatosis, and the lesions previously classified as desmoid tumors.

Most of the "desmoid" lesions involve skeletal muscle and associated fascial layers. They most frequently occur in women, in the abdominal wall, during or following pregnancy, but they are almost as common in men and in extra-abdominal sites, including the head and neck, thigh, and shoulder.

Lesions occasionally arise in surgical scars and in the mesenteries, and a familial from is associated with Gardner's syndrome. Wide excision with a margin of normal tissue is the recommended treatment. However, extremities and major vessels and nerves should be spared even if recurrence is likely. Local recurrences are common, and re-excision is often required. These lesions may also respond to radiation therapy. Some cases have responded to treatment with tamoxifen. However, there is still need for additional therapies.

SUMMARY OR THE INVENTION

The invention provides methods for inhibiting musculoaponeurotic fibromatoses in mammals by administering to the mammal in need thereof of an effective amount of a compound of formula I.

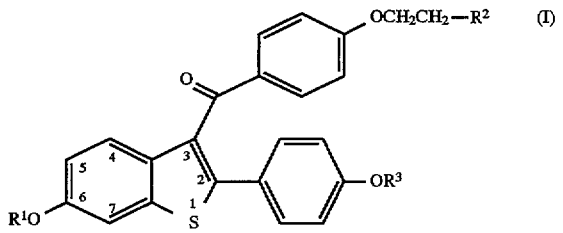

wherein $R^1$ and $R^3$ are independently hydrogen,

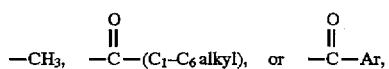

wherein Ar is optionally substituted phenyl;

$R^2$ is selected from the group consisting of pyrrolidino, hexamethyleneimino, and piperidino; and pharmaceutically acceptable salts and solvates thereof.

DETAILED DESCRIPTION OF THE INVENTION

The current invention concerns the discovery that a select group of 2-phenyl-3-aroylbenzothiophenes (benzothiophenes), those of formula I, are useful for inhibiting musculoaponeurotic fibromatoses.

The methods of use provided by this, invention are practiced by administering to a human in need thereof a dose of a compound of formula I or a pharmaceutically acceptable salt or solvate thereof, that is effective to inhibit musculoaponeurotic fibromatoses. The term "inhibit" includes its generally accepted meaning which includes prohibiting, preventing, restraining, and slowing, stopping, or reversing progression, severity, or a resultant symptom or effect.

Raloxifene, a compound of this invention wherein it is the hydrochloride salt of a compound of formula 1, $R^1$ and $R^3$ are hydrogen and $R^2$ is 1-piperidinyl, is a nuclear regulatory molecule. Raloxifene has been shown to bind to the estrogen receptor and was originally thought to be a molecule whose function and pharmacology was that of an anti-estrogen in that it blocked the ability of estrogen to activate uterine tissue and estrogen dependent breast cancers. Indeed, raloxifene does block the action of estrogen in some cells; however in other cell types, raloxifene activates the same genes as estrogen does and displays the same pharmacology, e.g., osteoporosis, hyperlipidemia. As a result, raloxifene has been referred to as an anti-estrogen with mixed agonist-antagonist properties. The unique profile which raloxifene displays and differs from that of estrogen is now thought to be due to the unique activation and/or suppression of various gene functions by the raloxifene-estrogen receptor complex as opposed to the activation and/or suppression of genes by the estrogen-estrogen receptor complex. Therefore, although raloxifene and estrogen utilize and compete for the same receptor, the pharmacological outcome from gene regulation of the two is not easily predicted and is unique to each.

Generally, the compound is formulated with common excipients, diluents or carriers, and compressed into tablets, or formulated as elixirs or solutions for convenient oral administration, or administered by the intramuscular or intravenous routes. The compounds can be administered transdermally, and may be formulated as sustained release dosage forms and the like.

The compounds used in the methods of the current invention can be made according to established procedures, such as those detailed in U.S. Pat. Nos. 4,133,814, 4,418,068, and 4,380,635 all of which are incorporated by reference herein. In general, the process starts with a benzo[b]thiophene having a 6-hydroxyl group and a 2-(4-hydroxyphenyl) group. The starting compound is protected, acylated, and deprotected to form the formula I compounds. Examples of the preparation of such compounds are provided in the U.S. patents discussed above. Optionally substituted phenyl includes phenyl and phenyl substituted once or twice with $C_1$–$C_6$ alkyl, $C_1$–$C_4$ alkoxy, hydroxy, nitro, chloro, fluoro, or tri(chloro or fluoro)methyl.

The compounds used in the methods of this invention form pharmaceutically acceptable acid and base addition salts with a wide variety of organic and inorganic acids and bases and include the physiologically acceptable salts which are often used in pharmaceutical chemistry. Such salts are also part of this invention. Typical inorganic acids used to form such salts include hydrochloric, hydrobromic, hydroiodic, nitric, sulfuric, phosphoric, hypophosphoric and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, caprate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, terephthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzene-sulfonate, p-bromophenylsulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like. A preferred sale is the hydrochloride salt.

The pharmaceutically acceptable acid addition salts are typically formed by reacting a compound of formula I with an equimolar or excess amount of acid. The reactants are generally combined in a mutual solvent such as diethyl ether or benzene. The salt normally precipitates out of solution within about one hour to 10 days and can be isolated by filtration or the solvent can be stripped off by conventional means.

Bases commonly used for formation of salts include ammonium hydroxide and alkali and alkaline earth metal hydroxides, carbonates, as well as aliphatic and primary, secondary and tertiary amines, aliphatic diamines. Bases especially useful in the preparation of addition salts include ammonium hydroxide, potassium carbonate, methylamine, diethylamine, ethylene diamine and cyclohexylamine.

The pharmaceutically acceptable salts generally have enhanced solubility characteristics compared to the compound from which they are derived, and thus are often more amenable to formulation as liquids or emulsions.

Pharmaceutical formulations can be prepared by procedures known in the art. For example, the compounds can be formulated with common excipients, diluents, or carriers, and formed into tablets, capsules, suspensions, powders, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinyl pyrrolidone; moisturizing agents such as glycerol; disintegrating agents such as calcium carbonate and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols.

The compounds can also be formulated as elixirs or solutions for convenient oral administration or as solutions appropriate for parenteral administration, for instance by intramuscular, subcutaneous or intravenous routes. Additionally, the compounds are well suited to formulation as sustained release dosage forms and the like. The formulations can be so constituted that they release the active ingredient only or preferably in a particular part of the intestinal tract, possibly over a period of time. The coatings, envelopes, and protective matrices may be made, for example, from polymeric substances or waxes.

The particular dosage of a compound of formula I required to inhibit musculoaponeurotic fibromatoses, or any other use disclosed herein, and according to this invention will depend upon the severity of the condition, the route of administration, and related factors that will be decided by the attending physician. Generally, accepted and effective daily doses will be from about 0.1 to about 1000 mg/day, and more typically from about 50 to about 200 mg/day. Such dosages will be administered to a subject in need thereof from once to about three times each day, or more often as needed to effectively inhibit musculoaponeurotic fibromatoses.

It is usually preferred to administer a compound of formula I in the form of an acid addition salt, as is customary in the administration of pharmaceuticals bearing a basic group, such as the piperidino ring. It is also advantageous to administer such a compound by the oral route. For such purposes the following oral dosage forms are available.

For topical administration, the compounds may be formulated as is known in the art for direct application to an area. Conventional forms for this purpose include ointments, lotions, pastes, jellies, sprays, and aerosols. The percent by weight of a compound of the invention present in a topical formulation will depend on various factors, but generally will be from 0.5% to 95% of the total weight of the formulation, and typically 1–25% by weight.

The compositions can take the form of an aqueous or anhydrous solution or dispersion, or alternatively the form of an emulsion or suspension.

These compositions can contain pharmaceutically acceptable vehicles and adjuvants which are well known in the prior art. It is possible, for example, to prepare solutions using one or more organic solvent(s) that is/are acceptable from the physiological standpoint, chosen, in addition to water, from solvents such as acetone, ethanol, isopropyl alcohol, glycol ethers such as the products sold under the name "Dowanol", polyglycols and polyethylene glycols, $C_1$–$C_4$ alkyl esters of short-chain acids, preferably ethyl or isopropyl lactate, fatty acid triglycerides such as the products marketed under the name "Miglyol", isopropyl myristate, animal, mineral and vegetable oils and polysiloxanes.

The compositions according to the invention can also contain thickening agents such as cellulose and/or cellulose derivatives. They can also contain gums such as xanthan, guar or carob gum or gum arabic, or alternatively polyethylene glycols, bentones and montmorillonites, and the like.

The galenical forms chiefly conditioned for topical application take the form of creams, milks, gels, dispersions or microemulsions, lotions thickened to a greater or lesser extent, impregnated pads, ointments or sticks, or alternatively the form of aerosol formulations in spray or foam form or alternatively in the form of a cake of soap.

FORMULATIONS

In the formulations which follow, "Active ingredient" means a compound of formula I.

Formulation 1

Gelatin Capsules

Hard gelatin capsules are prepared using the following:

| Ingredient | Quantity (mg/capsule) |
| --- | --- |
| Active ingredient | 0.1–1000 |
| Starch, NF | 0–650 |
| Starch flowable powder | 0–660 |
| Silicone fluid 350 centistokes | 0–15 |

The ingredients are blended, passed through a No. 45 mesh U.S. sieve, and filled into hard gelatin capsules.

Examples of specific capsule formulations of raloxifene that have been made include those shown below:

FORMULATION 2

Raloxifene capsule

| Ingredient | Quantity (mg/capsule) |
|---|---|
| Raloxifene | 1 |
| Starch, NF | 112 |
| Starch flowable powder | 225.3 |
| Silicone fluid 350 centistokes | 1.7 |

FORMULATION 3

Raloxifene capsule

| Ingredient | Quantity (mg/capsule) |
|---|---|
| Raloxifene | 5 |
| Starch, NF | 108 |
| starch flowable powder | 225.3 |
| Silicone fluid 350 centistokes | 1.7 |

FORMULATION 4

Raloxifene capsule

| Ingredient | Quantity (mg/capsule) |
|---|---|
| Raloxifene | 10 |
| Starch, NF | 103 |
| Starch flowable powder | 225.3 |
| Silicone fluid 350 centistokes | 1.7 |

FORMULATION 5

Raloxifene capsule

| Ingredient | Quantity (mg/capsule) |
|---|---|
| Raloxifene | 50 |
| Starch, NF | 150 |
| Starch flowable powder | 397 |
| Silicane fluid 350 centistokes | 3.0 |

The specific formulations above may be changed in compliance with the reasonable variations provided.

A tablet formulation is prepared using the ingredients below:

FORMULATION 6

Tablets

| Ingredient | Quantity (mg/tablet) |
|---|---|
| Active ingredient | 0.1–1000 |
| Cellulose, microcrystalline | 0–650 |
| Silicon dioxide, fumed | 0–650 |
| Stearate acid | 0–15 |

The components are blended and compressed to form tablets.

Alternatively, tablets each containing 0.1–1000 mg of active ingredient are made up as follows:

FORMULATION 7

Tablets

| Ingredient | Quantity (mg/tablet) |
|---|---|
| Active ingredient | 0.1–1000 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions each containing 0.1–1000 mg of medicament per 5 mL dose are made as follows:

FORMULATION 8

Suspensions

| Ingredient | Quantity (mg/5 ml) |
|---|---|
| Active ingredient | 0.1–1000 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified water to | 5 mL |

The medicament is passed through a No. 45 mesh U.S. sieve and mixed with the sodium carboxymethyl cellulose and syrup to form a smooth paste. The benzoic acid solution, flavor, and color are diluted with some of the water and added, with stirring. Sufficient water is then added to produce the required volume.

The following topical compositions are prepared:

FORMULATION 9

| Ingredient | Quantity (mg/5 ml) |
|---|---|
| Hydroxypropylcellulose | 1.5 g |
| Active Ingredient | 1.5–30 g |
| Isopropanol qs | 100 g |

FORMULATION 10

| Ingredient | Quantity (mg/5 ml) |
|---|---|
| Hydroxypropylcellulose | 1.5 g |
| Ethyl lactate | 15.0 g |
| Active Ingredient | 1.5–30 g |
| Isopropanol qs | 100 g |

FORMULATION 11

| Ingredient | Quantity (mg/5 ml) |
|---|---|
| Hydroxypropylcellulose | 1.0 g |
| Butylated hydroxytoluene | 0.02 g |
| Active Ingredient | 1.5–25 g |
| Ethanol qs | 100 g |

FORMULATION 12

| Ingredient | Quantity (mg/5 ml) |
|---|---|
| Hydroxypropylcellulose | 1.5 g |
| Butylated hydroxytoluene | 0.01 g |
| $C_8$–$C_{12}$ fatty acid triglycerides | 10.0 g |
| Active Ingredient | 1.5–30 g |
| Isopropanol qs | 100 g |

Formulation 9–12 take the form of gels.

FORMULATION 13

| Ingredient | Quantity (mg/5 ml) |
|---|---|
| Isopropanol | 46.0 g |
| Active Ingredient | 1.0–15 g |
| $C_8$—$C_{12}$ fatty acid triglycerides | 49.0 g |

FORMULATION 14

| Ingredient | Quantity (mg/5 ml) |
|---|---|
| Ethanol | 69.0 g |
| Ethyl lactate | 10.0 g |
| Active Ingredient | 1.5–20 g |
| $C_8$–$C_{12}$ fatty acid triglyceride | 30.0 g |

FORMULATION 15

| Ingredient | Quantity (mg/5 ml) |
|---|---|
| Isopropanol | 47.0 g |
| Acetone | 10.0 g |
| Ethyl lactate | 10.0 g |
| Active Ingredient | 1–15 g |
| $C_8$–$C_{12}$ fatty acid triglycerides | 30.0 g |

FORMULATION 16

| Ingredient | Quantity (mg/5 ml) |
|---|---|
| Ethanol | 95.08 g |
| Butylated hydroxytoluene | 0.02 g |
| Active Ingredient | 1.5–25 g |

Formulations 13, 14, 15, and 16 take the form of lotions.

FORMULATION 17

| Ingredient | Quantity (mg/5 ml) |
|---|---|
| White vaseline | 50.0 g |
| Liquid paraffin | 15.0 g |
| Refined paraffin wax | 32.0 g |
| Active Ingredient | 1–20 g |

FORMULATION 18

| Ingredient | Quantity (mg/5 ml) |
|---|---|
| White vaseline | 50.0 g |
| Liquid paraffin | 13.0 g |
| Refined paraffin wax | 32.0 g |
| Active Ingredient | 1–20 g |

Formulations 17 and 18 take the form of sticks

Desmoid tumors are rare non metastatic tumors of fibrous origin. Clinical correlates suggest that steroid hormones may have a role in the natural history of these tumors: it is predominantly seen in female patients of child-bearing age and regression of these tumors have been associated with menopause or with antiestrogen therapy.

The aim of this work was to identify estrogen receptors in desmoid tumor primary cells, and to evaluate the effect of a compound of formula I on desmoid cells in primary culture.

Because sometimes desmoid tumors develop in patients with Familial Adenomatous Polyposis (FAP), that can degenerate in colon or rectal cancer, we have tested the inhibitory effect of Compound Ia on cellular growth of an adenocarcinoma cell line, (HCT8), and fibroblasts from colon cancer bioptic specimens.

Compound Ia is a compound of formula I wherein $R^2$ is pyrrolidino, and $R^1$ and $R^3$ are hydrogen.

Binding studies are performed using intact cells. Desmoid cells are plated on 6-well plates in growth medium (Coon's modified Ham's F12 supplemented with 10% FCS). After 24 hours, the growth medium is substituted with steady state medium without phenol red, and cells are maintained in starvation for 24 hours. Then cells are incubated for one hour with 1 ml of medium without phenol red containing 25 mM HEPES and 0.5% EtOH (binding buffer) and increasing concentrations (0.05–10 nM) of [$^3$H]17$\beta E_2$ with or without a 500-fold excess of unlabeled 17$\beta E_2$ and Compound Ia. After incubation, cells are washed two times with 800 µl of binding buffer and lysed with 1N NaOH at 70° C for 30 minutes. Four N HCl is then added to each well for neutralization. Radioactivity is measured by liquid scintillation spectroscopy. ER binding affinity and binding-capacity are evaluated by Scatchard analysis.

All subsequent steps are performed at 0°–4° C. The pulverized tissue is homogenized with two 10-sec burst in a polytron homogenizer separated by a 30-sec cooling period in the following buffer: 10 mM Tris-HCl, 5 mM EDTA, 10 mM sodium molybdate, 10 mM dithiothreitol, 10% glycerol (v/v), pH 7.4. The homogenate is centrifuged at 7000 g for 20 min and the pellet is discarded, the supernatant was recentrifuged at 105000 g for 60 min to obtain cytosol for estrogen receptor analysis. Cytosol is diluted to 1–2 mg protein/ml. Cytosol protein is determined according to the method of Bradford. For estrogen receptor assessment, cytosol is incubated for 16 hr at 4° C. over a concentration range of 0.05–5 nM of [$^3$H]17$\beta E_2$ with or without a 500-fold excess of unlabeled 17$\beta E_2$ and Compound Ia. ER binding affinity and binding capacity are evaluated by Scatchard analysis.

Cells are plated on 6 well plates at a density of $8\times10^4$ cell for well in growth medium. After 24 hours, the cells are stimulated in growth medium without phenol red supplemented with 0.1% DMF, 0.1% EtOH, and different concentrations of Compound Ia ($2\times10^{-5}$M, $10^{-5}$M, $5\times10^{-6}$ M, $10^{-6}$M).

Cells are incubated six days, detached with trypsin/ethylenediamine tetracetic acid solution and then the growth is evaluated by counting to the microscope. The same method is used for colon cancer primary fibroblasts cell line and for HCT8 cell line: this line is cultured in RPMI and incubated 4 days after stimulation.

Collagen type I in culture media and cell layers are measured using an enzyme-linked immunoassay (ELISA). Briefly, cells are incubated for 24 hrs in supplement-free Coon's modified Ham F12 medium containing 50 µg/ml ascorbic acid and 100 µg/ml βaminopropionitryl fumarate.

Culture media are harvested and appropriately diluted in 0.1M carbonate/bicarbonate buffer (pH 9.6) and then used for coating the ELISA plates, overnight at $4°$ C. ELISA plates are incubated 1.5 hrs at $37°$ C. in PBS containing 5% of milk powder (PBS Blotto) to saturate non specific binding sites, 2 hrs at $37°$ C. with PBS Blotto containing the specific polyclonal antibody, and 1.5 hrs at $37°$ C. in PBS Blotto containing goat antirabbit IgG-alkaline phosphatase conjugated complex (Sigma Chemical Co., St. Louis, Mo.).

Samples are then exposed to 10% diethanolamine (pH 9.8) with 50 µg/ml Mg++ and 1 mg/ml paranitrophenylphosphate as a substrate of alkaline phosphatase at room temperature. Optical density is read at 405 nM, and concentrations calculated on the basis of the standard curve. Cell monolayers are harvested in 0.5N NaOH and sonicated to determine cellular Collagen type I. Cell extracts are then diluted in 0.1M carbonate/bicarbonate buffer (pH 9.6) and used for the coating of the ELISA plates. Standards and samples are assayed in triplicate. Results are expressed as µg protein/µg cellular DNA. DNA content is spectrofluorimetrically measured.

Binding experiments are performed using [$^3$H]17βE$_2$ as ligand in primary desmoid tumors cells and in frozen specimens of desmoid tumor.

In both experiments, [$^3$H]17βE$_2$ binding was slightly (approximately 10%) displaced by 500-fold excess of both unlabeled estrogen and Compound Ia. Scatchard analysis of [$^3$H]17βE$_2$ binding data using the computer binding program LIGAND (Munson P. J., Rodbard D. Anal. *Biochem.* 1980; 107:220–39.) shows the presence of ER in three different cultures and in two different cytosol preparation from bioptic specimens of desmoid tumors.

results are obtained with the HCT8 cell line (Table 2) and with a colon cancer fibroblastic cell line (Table 3).

Desmoid cells are inhibited in a dose-dependent fashion by Compound Ia at concentrations of $10^{-5}$M, $5\times10^6$M, $10^6$M, with maximal inhibitory effect at $10^{-5}$M concentration (Table 4).

Compound Ia is able to displace 17βE$_2$ binding to desmoid tissue only at very high concentrations (500-fold excess).

Compound Ia is able to significantly inhibit desmoid cell proliferation at micromolar concentrations. In addition, at similar concentrations the compound inhibits the proliferation of epithelial and fibroblastic cells derived from human colon cancer.

Type I collagen production is also significantly reduced in desmoid cell in primary culture by the Compound Ia.

At all the conditions (electroporation, Ca/P precipitation, lyposomes) tested for transfection of desmoid cells with the estrogen responsive elements, the cells are damaged, resulting not suitable for "in vitro" analysis.

TABLE 1

| Compound Ia (Mol/L) | Cell $\times 10^{-4}$ |
| --- | --- |
| Control | 12.3 |
| $2 \cdot 10^{-5}$ | 0.1 |
| $10^{-5}$ | 2.8 |
| $5 \cdot 10^{-6}$ | 7.0 |
| $10^{-6}$ | 10.0 |

TABLE 2

| Compound Ia (Mol/L) | Cell $\times 10^{-4}$ |
| --- | --- |
| Control | 150 |
| $2 \cdot 10^{-5}$ | 3 |
| $10^{-5}$ | 71 |
| $5 \cdot 10^{-6}$ | 115 |

TABLE 3

| Compound Ia (Mol/L) | Cell $\times 10^{-4}$ |
| --- | --- |
| Control | 7.6 |
| $2 \cdot 10^{-5}$ | 0.1 |
| $10^{-5}$ | 5.4 |
| $5 \cdot 10^{-6}$ | 6.3 |
| $10^{-6}$ | 7.6 |

TABLE 4

| | DNA (O:D.) | DNA (µg) | Collagen Type I (pg/well) | Collagen Type I (µg/µg DNA) | P values |
| --- | --- | --- | --- | --- | --- |
| Control | 4.85 ± 0.32 | 1.36 ± 0.06 | 47.82 ± 4.15 | 35.00 ± 1.41 | |
| Compound Ia 1 µM | 8.20 ± 0.23 | 1.97 ± 0.05 | 43.78 ± 5.23 | 22.00 ± 1.46 | P <0.005 |
| Compound Ia 5 µM | 6.90 ± 0.50 | 1.85 ± 0.24 | 38.01 ± 6.24 | 20.50 ± 0.61 | P <0.005 |
| Compound Ia 10 µM | 7.90 ± 1.46 | 1.96 ± 0.29 | 35.16 ± 2.44 | 18.00 ± 1.41 | P <0.005 |

In the growth assay, desmoid tumors primary cells are stimulated when exposed to various concentrations of Compound Ia. The result is a cellular growth inhibition with increasing Compound Ia concentrations (Table 1). Similar

We claim:

1. A method of inhibiting musculoaponeurotic fibromatoses comprising administering to a mammal in need thereof an effective amount of a compound having the formula

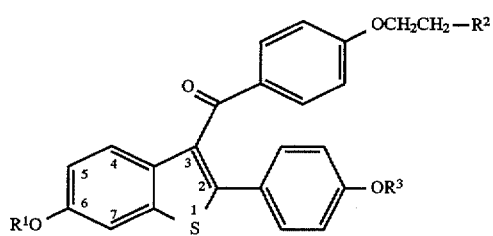

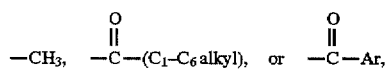

wherein $R^1$ and $R^3$ are independently hydrogen, $-CH_3$, $-\overset{O}{\underset{\|}{C}}-(C_1-C_6\text{alkyl})$, or $-\overset{O}{\underset{\|}{C}}-Ar$, wherein Ar is optionally substituted phenyl;
$R^2$ is selected from the group consisting of pyrrolidine, hexamethyleneimino, and piperidino; or a pharmaceutically acceptable salt of solvate thereof.

2. The method of claim 1 wherein said mammal is a human.

3. The method of claim 2 wherein said compound is the hydrochloride salt thereof.

4. The method of claim 3 wherein said compound is

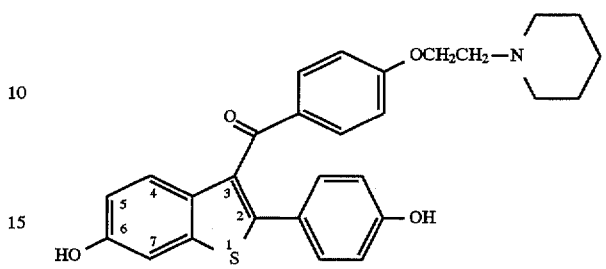

or its hydrochloride salt.

* * * * *